United States Patent
Hu et al.

(10) Patent No.: US 10,812,648 B2
(45) Date of Patent: Oct. 20, 2020

(54) CONTEXT-BASED NOTIFICATION

(71) Applicant: Hewlett-Packard Development Company, L.P., Spring, TX (US)

(72) Inventors: Michael W. Hu, Vancouver, WA (US); Shawn Richard Piper, Vancouver, WA (US); Brian Spate, Houston, TX (US); Juli Unger, Vancouver, WA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/342,676

(22) PCT Filed: Oct. 24, 2016

(86) PCT No.: PCT/US2016/058439
§ 371 (c)(1),
(2) Date: Apr. 17, 2019

(87) PCT Pub. No.: WO2018/080424
PCT Pub. Date: May 3, 2018

(65) Prior Publication Data
US 2020/0053200 A1    Feb. 13, 2020

(51) Int. Cl.
*H04M 1/725*    (2006.01)
*H04W 4/21*    (2018.01)
(Continued)

(52) U.S. Cl.
CPC ........ *H04M 1/72569* (2013.01); *G04G 9/007* (2013.01); *H04M 1/7253* (2013.01); *H04M 19/045* (2013.01); *H04W 4/21* (2018.02)

(58) Field of Classification Search
CPC ........... H04M 1/72569; H04M 1/7253; H04M 19/045; G04G 9/007; G04G 9/10;
(Continued)

(56) References Cited

U.S. PATENT DOCUMENTS 7,975,015 B2   7/2011   Horvitz et al.
8,948,821 B2   2/2015   Newham et al.
(Continued)

FOREIGN PATENT DOCUMENTS

EP   3032486    *   6/2016
EP   3032486 A1      6/2016

OTHER PUBLICATIONS

Corno, F., et al, A Context and User Aware Smart Notification System, Jan. 2016, < http://porto.polito.it/2627751/1/smartnotifications_preprint.pdf >.
(Continued)

*Primary Examiner* — Inder P Mehra
(74) *Attorney, Agent, or Firm* — Dicke Billig & Czaja PLLC (57) ABSTRACT

A device includes a context engine and a notification engine. The context engine determines a context indicator relative to received input while the notification engine selects, based on the context indicator and the received input, at least one type of notification from different types of notifications. A wearable electronic arrangement selectively communicates, and senses for different types of single user response to, at least a portion of the received input via the selected type of notification. The context engine receives feedback regarding the sensible different types of single user response to at least partially determine the context indicator.

20 Claims, 4 Drawing Sheets

(51) Int. Cl.
*G04G 9/00* (2006.01)
*G04G 21/00* (2010.01)
*G04G 9/10* (2006.01)
*A61B 5/021* (2006.01)
*A61B 5/00* (2006.01)
*A61B 5/01* (2006.01)
*A61B 5/053* (2006.01)
*H04M 19/04* (2006.01)

(58) Field of Classification Search
CPC ....... G04G 21/00; G04G 9/0064; H04W 4/21;
H04W 4/80; G04C 17/0091; A61B 5/021;
A61B 5/6898; A61B 5/7475; A61B
5/742; A61B 2503/12; A61B 2560/0242;
A61B 5/681; A61B 5/01; A61B 5/0533;
A61B 5/02405; A61B 5/002; A61B
5/02055; G06Q 50/01; H04L 67/26;
H04L 67/22
USPC .......................................................... 455/418
See application file for complete search history.

(56) References Cited

U.S. PATENT DOCUMENTS

| | | |
|---|---|---|
| 2004/0128359 A1 | 7/2004 | Horvitz |
| 2011/0264528 A1 | 10/2011 | Whale |
| 2014/0344375 A1 | 11/2014 | Hauser et al. |
| 2016/0000385 A1* | 1/2016 | Petersen ................ G08B 21/02 600/301 |
| 2016/0034424 A1* | 2/2016 | Won .................. H04M 1/72569 715/273 |
| 2016/0085397 A1* | 3/2016 | Jain ....................... G06F 3/0488 715/828 |
| 2016/0094936 A1* | 3/2016 | Yang ....................... H04Q 9/00 455/456.1 |
| 2017/0257483 A1* | 9/2017 | Bridge .................... H04W 4/21 |

OTHER PUBLICATIONS

For Smartwatches to Hit It Big, Context Is Key, Jun. 23, 2014, < http://time.com/2910318/for-smartwatches-to-hit-it-big-context-is-key/ >.

* cited by examiner

FIG. 9

CONTEXT-BASED NOTIFICATION

BACKGROUND

Electronics have revolutionized the development of information and its communication. Electronic communication may be visual, auditory, etc. and may occur via a wide variety of devices. Some forms of electronic communication involves telephony.

DETAILED DESCRIPTION

At least some examples of the present disclosure are directed to selectively communicate notifications to a user at least partially based on a social context. By doing so, a notification is made which is appropriate to the social context in which the user is present, such that the notification is not unduly obtrusive yet noticeable enough to the user for the relative importance or urgency of the message in the notification. If a notification is to be made in a sensitive social situation, it can be implemented in a manner to be relatively incomprehensible or unnoticeable by others. In some instances, some notifications may be delayed (e.g. sent at a later time) or even may be suppressed completely (e.g. not sent at all). These actions may minimize the volume, frequency, and intensity of an unrestricted flow of notifications on a single device or multiple devices of the user, which may be annoying and/or inappropriate to the social context in which the user is present.

In some examples, prior to making a selectively communicated notification to a user, a social context is at least partially determined by environmental parameter(s) and/or by a physiologic parameter(s) regarding the user. In some instances, sensors are used to determine some of the environmental parameters and/or physiologic parameters of the user at the time the received input occurs. In some examples, such sensors also may be used to at least partially to distinguish and determine the different types (e.g. timing and manner) of the user responses to selectively communicated notifications, thereby further enhancing current and future determinations of social context.

Accordingly, instead of permitting automatic communication of every potential notification to a user, a notification device in accordance with examples of the present disclosure may enable judicious, context-appropriate communication of some notifications to the user. Stated differently, input received by the notification device is decoupled from its automatic output so that each piece of received input is communicated at an appropriate time and manner given the social context of the user, nature of the information, etc.

In some examples, a determination of a social context indicator may also be at least partially based on specific user responses to prior notifications, thereby increasing an accuracy of selecting the appropriate time and manner of selectively communicating future notifications to the user.

In some examples, at least some of the determination of whether and how a particular notification is selectively communicated may be performed in external locations, such the cloud (e.g. a web-based resource). In this way, less intensive computing resources and/or memory resources may be employed in electronic devices wearable by the user (and by which selective notifications are communicated).

This example, and additional examples, are described further in association with at least FIGS. 1-9.

Figure 1:
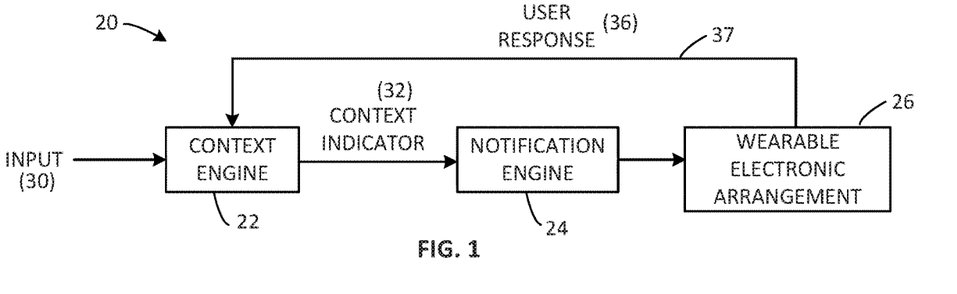
FIG. 1 is a block diagram schematically representing a notification device, according to one example of the present disclosure.

FIG. 1 is a block diagram schematically representing a notification device 20, according to one example of the present disclosure.

As shown in FIG. 1, a device 20 comprises a context engine 22, a notification engine 24, and a wearable electronic arrangement 26. The context engine 22 is to determine a context indicator 32 relative to received input while the notification engine 24 is to select, based on the context indicator and the received input, at least one type of notification from different types of notifications. In some examples, the context indicator 32 may comprise a social context indicator.

In some examples, the context indicator 32 comprises a quantitative score. In some examples, at least the context engine 22 and/or notification engine 24 may involve at least partially automated machine learning processes to determine the context indicator 32 (and related operations) in the manner described in the various examples of the present disclosure.

The wearable electronic arrangement 26 is to selectively communicate, and to sense for different types of single user response to, at least a portion of the received input via the selected type of notification. In some examples, this selective communication includes a decision not to communicate the received input to the single user or at least delaying the communication for a period of time, change in location, change in activity, etc.

In some examples, the context engine 22 is to receive feedback regarding the sensible different types of single user response 36 to at least partially determine the context indicator 32.

In some examples, device 20 may sometimes be referred to as a notification arrangement. In some instances, the received input may sometimes be referred to as an incoming notification and/or the selectively communicated notification may sometimes be referred to as an outgoing notification.

In some examples, the received input 30 comprises data 302 and/or a communication 304 as further illustrated later in association with FIG. 6. In some examples, the data 302 and/or communication 304 is received from an external source. In some examples, such data and/or communication (comprising the received input) may originate via a portion of the wearable electronic arrangement 26. It will be understood that the terms "data" and "communication" as used with respect to at least input 30 are not necessarily mutually exclusive regarding the type and manner of input 30.

In some examples, the received input 30 comprises a call notification (e.g. ringtone of incoming phone call), a short message system (SMS) notification (e.g. incoming text message), a weather update, a social media message from a particular source, or a third party "app" notification. In some instances, the SMS notification (e.g. text) may be from a particular person (e.g. family, spouse) as compared to an unknown sender, which then may determine the relative urgency of importance of communicating the information to the user. In some instances, the received input 30 may comprise data from a third party source conveying data or information regarding news, finance, sports, security, etc.

In some examples, at least the context engine 22 and/or notification engine 24 are embodied as machine readable instructions stored in a non-transitory memory and executable via a processing resource, as more fully described and illustrated later in association with at least FIG. 2.

As further shown in FIG. 1, in some examples, information regarding a user response 36 to a selectively communicated notification is fed back to the context engine. This information includes different types of a single user response to the different types of notifications relative to different types of the received input. In some examples, this feedback 37 may be used by the context engine 22 for determination of the context indicator 32 to sort future received input 30.

In some examples, a lack of acknowledgement (e.g. ignore) by the user may be considered one type of user response 36. Meanwhile, in some examples different forms of acknowledgement of a selectively communicated notification may be considered different types of user responses, such as further described later in association with at least FIG. 5.

With this in mind, in some examples the context engine 22 may access and/or store a history of different types of user responses to the different types of notifications in association with previous instances of the social context indicator and in association with the different types of the received input and/or different states of those received inputs. Moreover, based on the particular user's response over time, each of the different types of inputs, user responses, and other information (e.g. environmental conditions, physical state of user) may be weighted as part of the determination of the context indicator 32.

Figure 2:
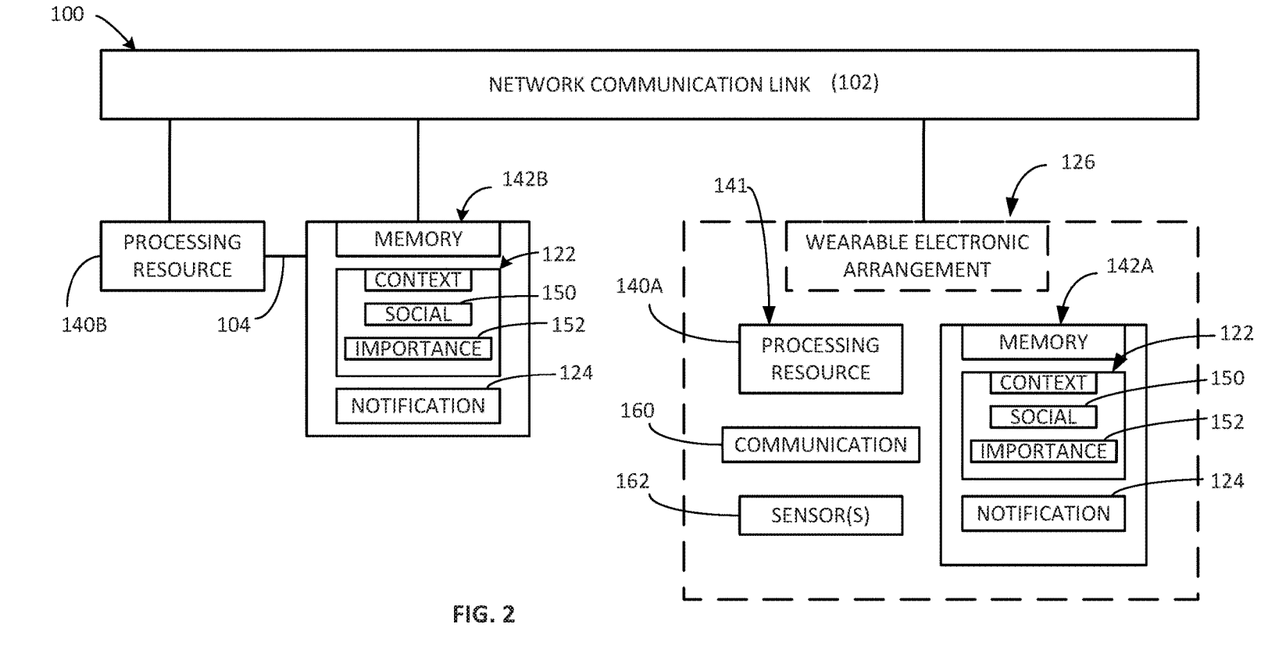
FIG. 2 is a block diagram schematically representing a notification device, according to one example of the present disclosure.

FIG. 2 is a block diagram schematically representing a notification device 100. In some examples, the notification device 100 comprises at least some of the substantially the same features as the notification device 20 in FIG. 1. In some examples, the notification device 100 comprises one example implementation of the notification device 20 in FIG. 1.

As shown in FIG. 2, the notification device 100 comprises at least one processing resource (140A, 140B) and at least one non-transitory memory (142A, 142B). In some examples, a processing resource 140A and/or a memory 142A comprises a portion of and/or is associated with a wearable electronic arrangement 126. In some examples, a processing resource 140B and/or a memory 142B may be external to the wearable electronic arrangement 126.

In some examples, the notification device 100 includes a network communication link 102 by which communication can occur between the respective external processing resource 140B and/or memory 142B and the respective processing resource 140A and/or memory 142A of wearable electronic arrangement 126. In some examples, the network communication link 102 may comprise a wired and/or wireless path, which may involve the internet, intranet, world wide web, local area network (LAN), wide area network (WAN), virtual private network (VPN), peer-to-peer, mobile telephony protocols, Bluetooth, NFC, etc.

In some examples, the external processing resource 140B and external memory 142B can communicate directly with each other at least partially via a link 104 while in some examples, the external processing resource 140B and memory 142B communicate with each other at least partially via network communication link 102.

As shown in FIG. 2, memory 142A, 142B stores instructions to implement a context engine 122 and a notification engine 124, with similar reference elements referring to similar elements 22 and 24 in FIG. 1. As further shown in FIG. 2, whether stored in memory 142A and/or in external memory 142B in some examples the context engine 122 includes and implements a social context parameter 150 and/or an importance parameter 152.

In some examples, the social context parameter 150 identifies and tracks information and cues to determine a social context of the user for determining a type and manner of selectively communicating a notification to user, if at all.

In some examples, the importance parameter 152 identifies and tracks a relative importance of received input, without necessarily identifying and tracking a social context in which the user is present.

In some examples, the social context parameter 150 is used without the importance parameter 152. In some examples, the importance parameter 152 may be used without the social context parameter 150. However, in some examples, a combination of the social context parameter 150 and the importance parameter 152 may be used together in a complementary manner to determine a context indicator 32.

In some examples, some portions of the content engine 122 and some portions of the notification engine 124 are stored in the external memory 142B and executed via the external processing resource 140B while some portions of the content engine 122 and some portions of the notification engine 124 are stored in memory 142A and executed via the processing resource 140A of a wearable electronic arrangement 126. In this way, operation of the content engine 122 and/or notification engine 124 may be distributed between an external resource (e.g. cloud processing and/or cloud memory) and the resources of the components of the wearable electronic arrangement 126. In some examples, via such arrangement 126, more intensive computing tasks can be performed external to the wearable electronic arrangement 126, thereby simplifying the design, implementation, size, etc. of the wearable electronic arrangement 126.

As shown in FIG. 2, in some examples the wearable electronic arrangement 126 may comprise a communication element 160, which can selectively communicate a notification to a user of the wearable electronic arrangement 126. In some instances, a communication performed via the communication element 160 may sometimes be referred to as a notification.

As shown in FIG. 2, in some examples the wearable electronic arrangement 126 comprises sensor(s) 162. In some examples, at least some of the sensors 162 may sense environmental information and/or a user's physiologic information, as later further described in association with FIG. 6.

In some examples, this sensed environmental and/or physiologic information is used to at least partially determine the context indicator 32 (FIG. 1) in association with at least received input 30.

In some examples, sensor(s) 162 enable sensing and tracking a user response after receiving a selectively communicated notification from the communication element 160, with information regarding the user response then being communicated to the context engine 22 via a feedback path 37 (FIG. 1). In at least this way, at least some user response information is used in determining the context indicator 32. In some examples, the sensor(s) 162 may comprise circuitry and/or functionality to sense any one, or a combination of, different types of user responses, at least some of which are further described later in association with at least FIG. 5.

With further reference to at least FIG. 2, in some examples the processing resource 140A, 140B and memory 142A, 142B may form at least a portion of a control portion 141 to implement and/or manage any one of the devices, arrangements, engines, parameters, components, elements, operations, and/or functions associated with contextual notifications, as represented throughout the present disclosure in association with FIGS. 1-3 and 5-9.

With this in mind, processing resource 140A, 140B is electrically couplable to, and in communication with, memory 142A, 142B to generate control signals to direct operation of at least some the devices, arrangements, engines, parameters, components, elements, operations, and/or functions, as represented throughout the present disclosure. In some examples, these generated control signals include, but are not limited to, employing context and notification engines (e.g. 22, 24, 122, 124) stored as instructions in memory (e.g. 42, 142A, 142B) in the manner described in at least some examples of the present disclosure.

In some examples, processing resource 140A, 140B is embodied in a general purpose computing device (e.g. server) while in some examples, processing resource 140A, 140B is incorporated into or associated with at least some of the associated devices, arrangements, engines, parameters, components, elements, operations, and/or functions described throughout the examples of the present disclosure.

For purposes of this application, in reference to the processing resource 140A, 140B, the term "processing resource" shall mean a presently developed or future developed processing resources that executes sequences of machine readable instructions contained in a memory. In some instances, a processing resource may sometimes be referred to as a processor.

In some examples, execution of the sequences of machine readable instructions, such as those provided via memory 142A, 142B causes the processing resource to perform actions, such as implementing context notification as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 142A, 142B. In some examples, memory 142A, 142B comprises a computer readable tangible medium providing non-volatile storage of the machine readable instructions executable by a process of processing resource 140A, 140B. In other examples, hard wired circuitry may be used in place of or in combination with machine readable instructions to implement the functions described. For example, processing resource 140A, 140B may be embodied as part of at least one application-specific integrated circuit (ASIC). In at least some examples, the processing resource 140A, 140B is not limited to any specific combination of hardware circuitry and machine readable instructions, nor limited to any particular source for the machine readable instructions executed by the processing resource 140A, 140B.

Figure 3:
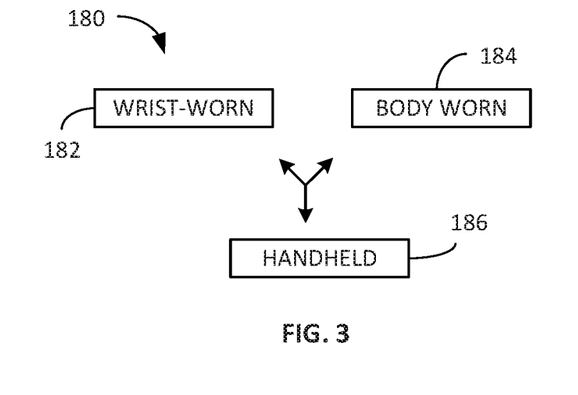
FIG. 3 is a block diagram schematically representing a wearable electronic arrangement, according to one example of the present disclosure.

FIG. 3 is a block diagram schematically representing a wearable electronic arrangement 180, according to one example of the present disclosure. In some examples, the wearable electronic arrangement 180 may comprise one example implementation of the wearable electronic arrangement 26, 126 (FIGS. 1-2).

As shown in FIG. 3, in some examples, the wearable electronic arrangement comprises a wrist-worn device 182, body-worn device 184, and/or a handheld device 186 which may be worn or carried on the body or otherwise generally associated with other wearable components such as 182, 184. In some examples, the body-worn device 184 may comprise components worn on the head or neck. In some examples, the body-worn device 184 may comprise a wearable ear piece. In some examples, the wrist-worn device 182 and/or body-worn device 184 may comprise a physiologic sensor (e.g. motion, EEG, audio, temperature, skin, etc.).

In some examples, via a single or multiple devices 182, 184, 186 of a wearable electronic arrangement 180, a range of different types of notifications (e.g. user notifications in FIG. 4) may be implemented to enhance a user in making a discrete response to a selectively communicated notification. In some examples, a single or multiple device 182, 184, 186 of a wearable electronic arrangement 126, may at least partially sense and/or record a range of different types of user responses (e.g. user notifications in FIG. 5) to a selectively communicated notification.

As shown in FIG. 3, in some examples the handheld device 186 of the wearable electronic arrangement 180 comprises a smart phone in short range wireless communication with a respective one of the wrist-worn device 182 and the body-worn device 184, with at least a portion of a memory (e.g. 140A) and at least a portion of the processing resource (142A) being located on the handheld device 186 (e.g. smart phone, tablet, etc.).

In some examples, the context engine 122 (FIG. 1) of a notification device may operate in a mobile app on a handheld device 186, such as a smartphone, with sensors 162 on the handheld device 186, wrist-worn device 182, and/or body-worn device 184 feeding environmental or physiologic information into the context engine 122.

Figure 4:
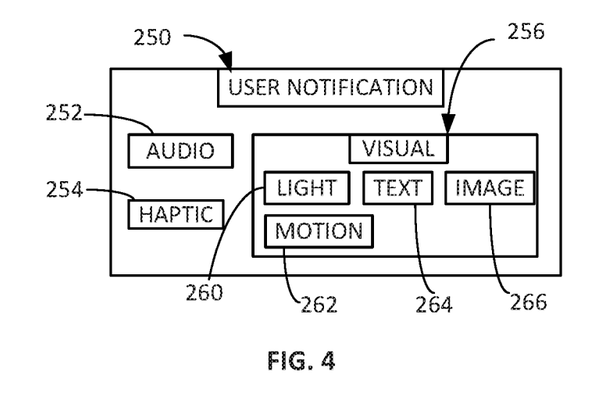
FIG. 4 is a block diagram schematically representing different types of user notifications, according to one example of the present disclosure.

FIG. 4 is a block diagram schematically representing a range 250 of different types of user notifications, according to one example of the present disclosure. In some examples, at least some of the user notifications represented in FIG. 4 may comprise example implementations of the notifications described in association with at least FIGS. 1-3 and FIGS. 5-9. As shown in FIG. 4, at least some example user notifications comprise an audio component 252, a haptic component 254, and/or a visual component 256.

In some examples, a user notification may exclude or omit an audio component 252, which in turn may minimize drawing the attention of others to the notification selectively communicated to the user. On the other hand, in some examples when it is socially appropriate, an audio component 252 may be specifically included, thereby increasing the probability of a prompt user response to a notification warranting a vigorous user response.

Any one of, or a combination of, the type of notification components 252, 254, 256 can be implemented continuously or in various intermittent patterns. Each different intermittent pattern may be associated with a particular urgency or relative importance and/or may be utilized in association with a particular range of scores of context indicator 32. In some examples, besides implementing different intermittent patterns, the different notification components 252, 254, 256 may comprise different selective levels of intensity, duration, etc. In some examples, such different patterns may be associated with different sources of information or different subjects of the information.

In some examples, the haptic component 254 comprises a vibratory element while in some examples, the haptic component 54 may comprise other tactile modalities.

In some examples, the visual component 256 comprises a lighting element 260, a motion element 262, a text element 264 and/or an image element 266. In some examples, the visual component 256 may be implemented via LEDs, e-paper, OLED, and/or modalities. In some examples, the visual component 256 may be expressed via a variable volume of info on a display and/or different colors corresponding to different types of information or corresponding to different levels of urgency associated with a selectively communicated notification.

In some examples, the notification engine 124 (FIG. 2) receives the context indicator 32 and determines by which type and manner any notification is to be selectively communicated to the user. In some examples, once it is determined that it is sufficiently appropriate to selectively communicate at least one notification, the notification engine 124 selects an audio component 252, a haptic component 254, and/or a visual component 256 from which the notification may be built. It will be understood that other selectable modalities of notifying a user are not excluded. Some example notifications comprise suppressing the notification completely or presenting a notification with both a haptic component 254 and a visual component 256. Some example notifications comprise presenting a notification including a haptic component 254 without a visual component 256 or a notification including a visual component 256 without a haptic component 254. In some examples in which a visual component 256 is presented (with or without a haptic component 254), the notification may comprise different lighting patterns, colors, durations, brightness via at least light element 260. In some examples in which a visual component 256 is presented, the respective text and image elements 264, 266 may comprise different volumes of information and/or different patterns on the display. It will be understood that in some examples, image elements 266 may comprise graphics, non-text character patterns, non-text shape patterns, etc. which may be continuous, intermittent, in series, random, etc.

Figure 5:
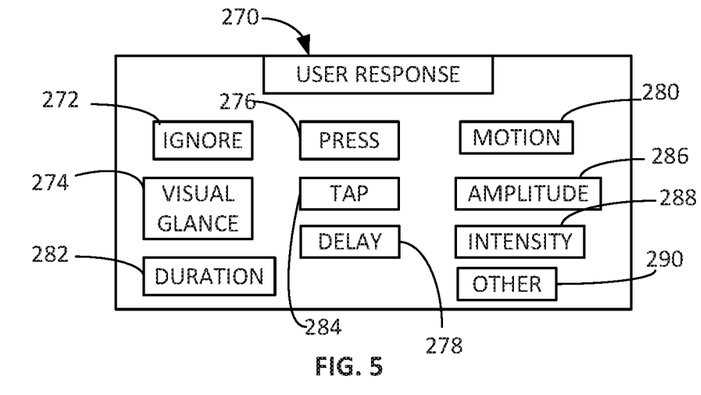
FIG. 5 is a block diagram schematically representing different types of user responses, according to one example of the present disclosure.

FIG. 5 is block diagram schematically representing a plurality 270 of different user responses to a selective communication from the notification engine 126, as consistent with at least some of substantially the same features and attributes as described in association with at least FIGS. 1-4 and 6-9.

As shown in FIG. 5, in some examples the different types of single user response relative to the selective communication comprise at least one of an ignore parameter 272, a visual glance parameter 274, press control parameter 276, tapping parameter 278, device movement parameter 280 (e.g. motion), device movement amplitude parameter 286, interaction duration parameter 282, delay parameter 284 (e.g. duration of delay before responding), response intensity parameter 288, and/or other parameter 290. In some examples, a user response to a selectively communicated notification may comprise any combination of various multiple different types of single user response (FIG. 5). It also will be understood that, in at least some instances, the term single user response refers to a user response specific to a particular user and not generic user responses.

In some examples, a user response may be direct or active, such as the user pressing a button (e.g. parameter 276) or the user abruptly getting up from a seated or prone position, which would be detectable per at least parameters 280, 286, and/or 288. In some examples, such abrupt movement may be detected via an accelerometer per parameter 280 as high intensity gross movement even when the user does not touch the device (e.g. parameter 276).

In some examples, a user response may be more passive such as merely turning their wrist (e.g. parameter 280) to look at the display but not pressing a button (e.g. parameter 276) or merely turning their head, as detectable via an earpiece (e.g. body worn device 184 in FIG. 3).

Figure 6:
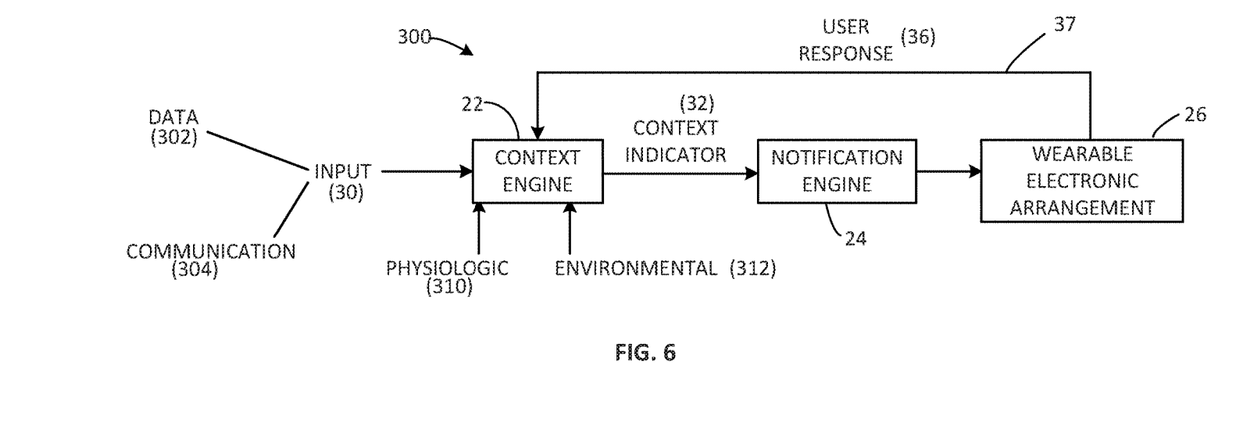
FIG. 6 is a block diagram schematically representing a notification device, according to one example of the present disclosure.

FIG. 6 is a block diagram schematically representing a notification device 300, according to one example of the present disclosure. In some examples, the notification device 300 comprises at least some of substantially the same features as notification device 20, 100 as previously described in association with at least FIGS. 1-5, and further comprising at least a physiologic parameter 310 and an environmental parameter 312.

As shown in FIG. 6, in some examples the context engine 22 may at least partially determine the context indicator 32 based on at least one physiologic parameter 310. In some examples, the physiologic parameter 310 may comprise a heart rate, heart rate variability, galvanic skin response, body temperature, mental state (e.g. electroencephalography EEG), body motion, amplitude or type of motion, body posture, blood pressure, etc. In some instances, such information is determined via a variety of sensors 162 (FIG. 2), such as an accelerometer, temperature sensor, etc. forming part of the wearable electronic arrangement 126 (FIG. 2) and/or in communication with the wearable electronic arrangement 126. In some examples, the physiologic parameter 310 may comprise general activity or step count, sleep quality, wellness or stress level. In one aspect, from this physiologic information the context engine 122 may infer what a user is doing (e.g. sleeping in bed, running outside, etc.) and/or their mental and physical state, particularly where such physiologic information is considered in combination with at least one environmental parameter 312 (e.g. time of day, geolocation, etc.) as further described below.

As shown in FIG. 6, in some examples, the context engine may at least partially determine the context indicator 32 based on at least one environmental parameter 312. In some examples, the environmental parameter 312 may comprise a time of day, a day of week, time until next event, a geolocation, and/or proximity to home or office or other location detectable by smartwatch or connected smartphone. In some examples, the environmental parameter 312 may comprise a proximity to a family member, co-worker, friend, etc. In some examples, the environmental parameter 312 may comprise whether the user is indoor or outdoor, as detectable via a light sensor, geolocation, etc. In some examples, the environmental parameter 312 may comprise general or specific weather conditions, such as temperature, humidity, barometric pressure, UV light, ambient light and spectrum. Such weather conditions may be sensed via components of the wearable electronic arrangement 126 and/or may be communicated via sources external to the wearable electronic arrangement 126. In some examples, the environmental parameter 312 may comprise ambient noise and/or noise frequencies.

In some examples, the environmental parameter 312 may comprise data such as smart home data (e.g. thermostat reading, on/off status for connected device) or other data such as a battery level of a component of the wearable electronic arrangement 126.

In some examples, the environmental parameter 312 may comprise a quantity of notifications available or a type of notification.

In some examples, the environmental parameter 312 to be fed to the context indicator 32 may comprise a non-user context parameter. In other words, the context indicator 32 may be at least partially based on information regarding persons other than the user wearing the wearable electronic arrangement 126. In some examples, the non-user social context parameter may be at least partially based on a geolocation (work, church, school, etc.) of the non-user and their proximity to the user. In some examples, the non-user social context parameter may be at least partially based on time.

In some examples, just one of the physiologic parameter 310 and the environmental parameter 312 is employed by the context engine 22 to determine the context indicator 32 while in some examples, both the respective physiologic and environmental parameters 310, 312 are employed in a complementary manner by the context engine 22.

Figure 7:
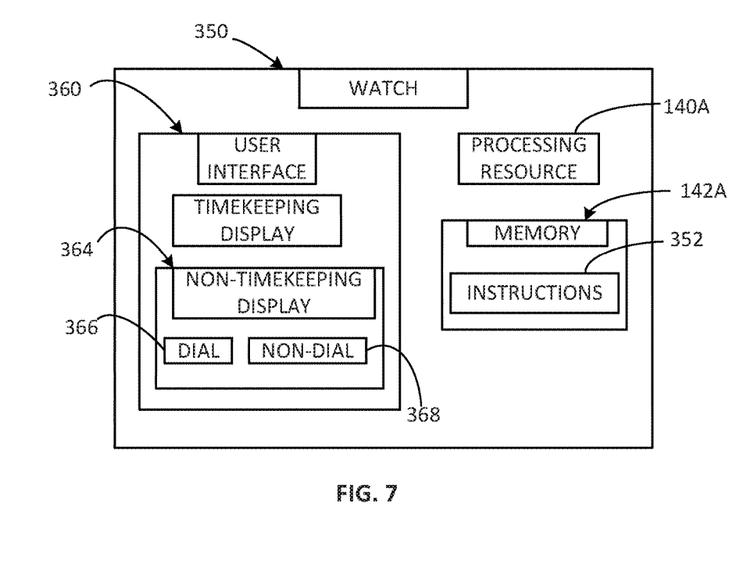
FIG. 7 is a block diagram schematically representing a wearable watch, according to one example of the present disclosure.

FIG. 7 is a block diagram schematically representing a wearable watch 350, according to one example of the present disclosure. In some examples, the watch 350 comprises at least some of substantially the same features and attributes as the notification devices 20, 100, 300 and/or wearable electronic arrangements 26, 126 as previously described in association with at least FIGS. 1-6. The watch 350 may comprise one example implementation of at least one component of the previously described wearable electronic arrangement 26, 126.

As shown in FIG. 7, in some examples a wearable watch 350 comprises a user interface 360 including a time-keeping display portion 362 and a non-time-keeping display portion 364. In some examples, the user interface 360 may comprise a display (e.g. face) of a watch. In some examples, watch 350 comprises a control portion 141 including a processing resource 140A to execute machine readable instructions 352 stored in a non-transitory memory 142A. Among other items, the instructions 352 may implement at least a context engine 22, 122 and/or notification engine 24, 124 as previously described in association with FIGS. 1-6.

In some examples, the time-keeping display portion 362 may be analog, digital, or a combination of analog and digital. Similarly, in some examples, the non-time-keeping display portion 364 may be analog, digital, or a combination of analog and digital.

In some examples, the time-keeping display portion 362 can indicate time of day, day of week, day of month, and the like.

In some examples, the non-time-keeping display portion 364 comprises a dial element 366, which may be juxtaposed relative to the time-keeping display portion 362. However, in some examples, the non-time-keeping display portion 364 comprises a non-dial element 368. Whether in the form of a dial element 366 or a non-dial element 368, the non-time-keeping display portion 364 may comprise an analog element (e.g. rotatable hands), a digital element (e.g. display screen), or a combination of analog and digital elements. The digital element 366 can comprise a light emitting diode (LED) display, an e-ink display or organic light emitting display (OLED), which can display text, icons, images, etc. in a static or dynamic manner. Whatever combination of analog and digital components are embodied as user interface 360, those respective components of the non-time-keeping display portion 364 may work in a complementary manner to provide information as a selectively communicated notification to the user.

In some examples in which the non-time-keeping display portion 364 is analog, such as at least one hand rotatable relative to a dial 366, a motion and/or position of the at least one hand is controllable via a processing resource (e.g. 140A).

In some examples, at least some features and attributes of the respective display portions 362, 364 are implemented in the watch display 380 as later described in association with at least FIG. 8.

In some examples, the wearable watch 350 comprises a wristwatch. In one aspect, a wristwatch 350 may enhance the discrete delivery, and response to, selectively communicated notifications according to a social context indicator. For instance, the location on the wrist may enable user observation of a notification without moving any other part of their body, and can enable responding (at least in some fashion) to the notification with minimal movement, thereby enabling the user to not draw attention to themselves in some social situations.

Figure 8:
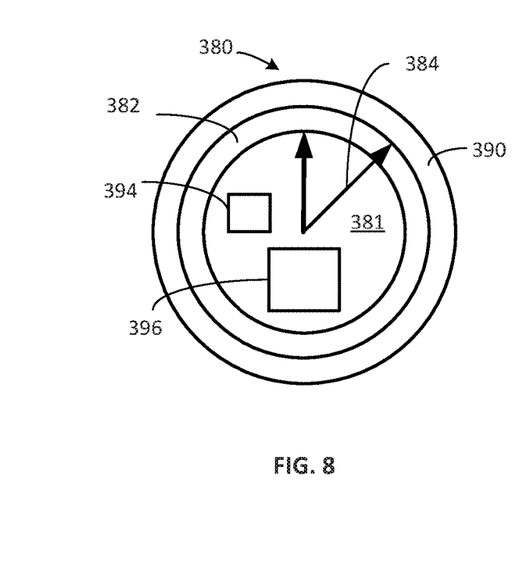
FIG. 8 is a block diagram schematically representing a watch display, according to one example of the present disclosure.

FIG. 8 is a top plan view schematically representing a watch display 380, in accordance with one example of the present disclosure. In some examples, the watch display 380 comprises at least some of the substantially the same features as the watch 350 (FIG. 7) and/or wearable electronic arrangements 26, 126 (FIGS. 1-6). In some examples, the watch display 380 comprises one example implementation of watch 350 (FIG. 7).

As shown in FIG. 8, in some examples watch display 380 comprises a face 381 having a first dial 382 relative to which hands 384 move to provide a time-keeping function. This arrangement may comprise one example implementation of the time-keeping display portion 362 in FIG. 7. In some examples, watch display 380 comprises at least one second dial 390, which may comprise one example implementation of the non-time-keeping display portion 364 in FIG. 7. Whether second dial 390 embodies an analog format, digital format or both, second dial 390 may implement at least some of the different types of user notifications (FIGS. 1-4) and/or enable at least some of the different types of user responses (FIG. 1-5).

In some examples, however, instead of or in addition to first dial 382 and hands 384, watch 380 includes a first digital portion 394 and/or a second digital portion 396 to implement a time-keeping function. While shown as a rectangle in FIG. 8, the respective first and second digital portions 394, 396 may take a variety of shape, sizes, and/or forms other than a rectangle and have locations on face 381 other than that shown in FIG. 8.

In some examples, at least one of the respective first and second display portions 394, 396 may be an example implementation of non-time-keeping display portion 364. In such examples, the first and second display portions 394, 396 may implement at least some of the different types of user notifications (FIGS. 1-4) and/or enable at least some of the different types of user responses (FIG. 1-5). In some examples, at least the second dial 390, display portions 394, 396 may express at least some aspects of the visual component 256 of a user notification as previously described in association with at least FIG. 4.

It will be understood that in some examples, various combinations of the respective dials 382, 390 and respective digital portions 394, 396 may be employed to implement user notifications and/or user responses.

Figure 9:
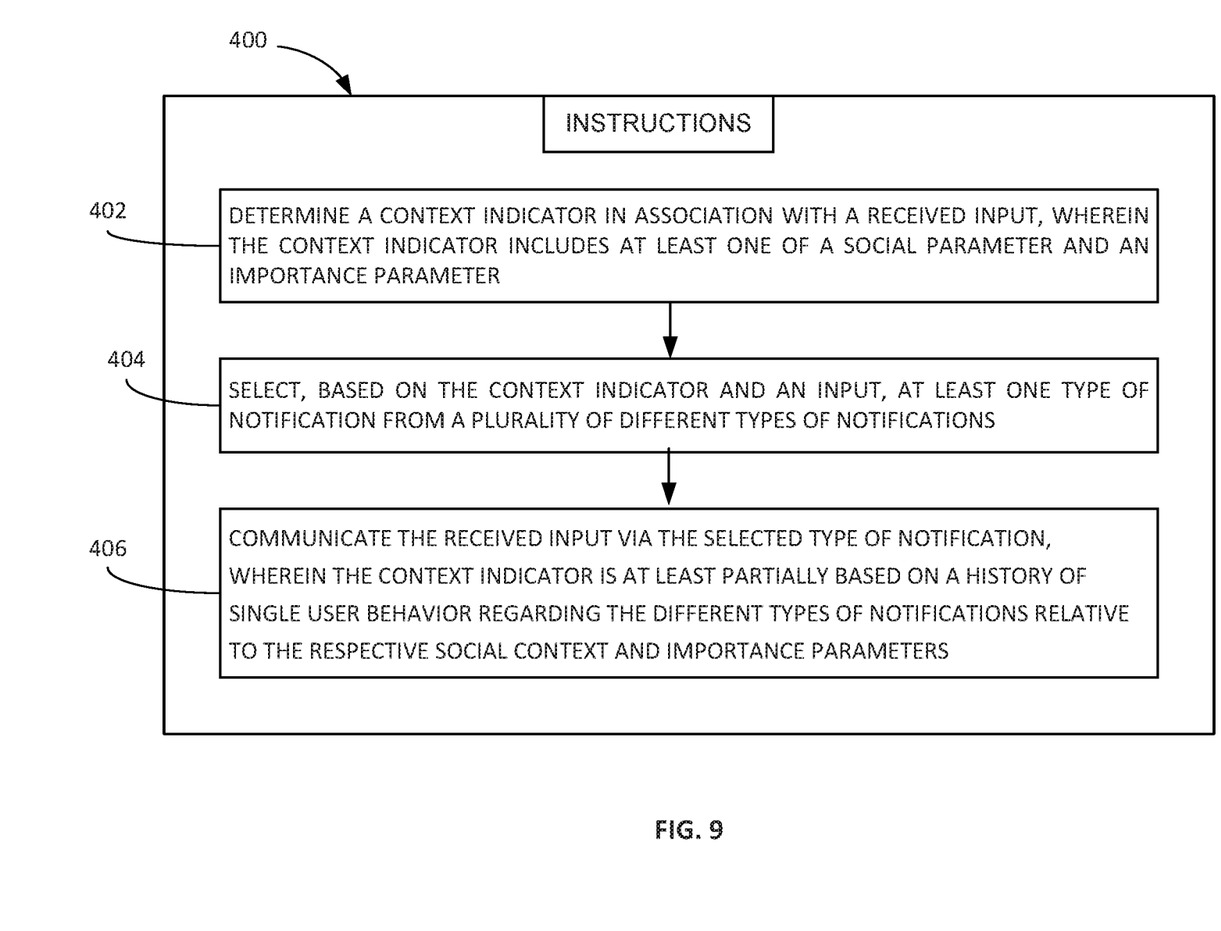
FIG. 9 is a block diagram schematically representing notification instructions, according to one example of the present disclosure.

FIG. 9 is a flow diagram schematically representing at least some instructions 400 executable via a processing resource (e.g. 140A and/or 140B) and storage in a non-transitory memory (e.g. 142A and/or 142B), according to one example of the present disclosure.

As shown in FIG. 9, the instructions include determining a context indicator in association with a received input, wherein the context indicator includes at least one of a social parameter and an importance parameter. Further instructions include selecting, based on the context indicator and an input, at least one type of notification from a plurality of different types of notifications. The received input is selectively communicated via the selected type of notification. The context indicator is at least partially based on a history of different single user behaviors regarding the different types of notifications relative to the respective social context and importance parameters. It will be understood that in some examples, upon receiving the same input, the context indicator may still evolve over time based on changes in the way the user responds differently over time to the same inputs (i.e. inputs which have not changed over time). In some examples, this tracked history also includes the different types of received input in association with the selectively communicated notifications and associated specific user responses.

The invention claimed is:

1. A device comprising:
non-transitory memory to store machine readable instructions, executable on a processing resource, to implement:
  a context engine to determine a social context indicator for a notification of a device based on a received input for the device, a social context of a user of the device at a time of the received input, and prior response of the user to different types of notifications for different types of received inputs in different social contexts; and
  a notification engine to select, based on the received input, the social context of the user, and the social context indicator, at least one type of notification from the different types of notifications; and
a wearable electronic arrangement to selectively communicate at least a portion of the received input to the user via the selected type of notification,
the wearable electronic arrangement to sense response of the user to the selected type of notification and the context engine to receive feedback regarding the sensed user response to at least partially determine the social context indicator based on the sensed user response to different types of notifications for different types of received inputs in different social contexts.

2. The device of claim 1, the context engine to determine the social context indicator based on at least one physiologic-related sensor parameter of the user sensed prior to the selective communication of the received input.

3. The device of claim 2, the at least one physiologic-related sensor parameter of the user to be sensed after the selective communication of the received input.

4. The device of claim 2, the context engine to further determine the social context indicator based on at least one environmental sensor parameter of the user sensed prior to the selective communication of the received input.

5. The device of claim 1, the context engine to determine the social context indicator based on at least one environmental parameter of the user.

6. The device of claim 1, wherein the received input is at least one of data and a communication received from an external source.

7. The device of claim 1, wherein at least a portion of non-transitory memory, and at least a portion of the processing resource, are located external to the wearable electronic arrangement.

8. The device of claim 1, wherein the wearable electronic arrangement comprises at least one of a wrist-worn device and a body-worn device.

9. The device of claim 8, wherein the wearable electronic arrangement comprises a smart phone in short range wireless communication with a respective one of the wrist-worn device and the body-worn device, and at least a portion of the non-transitory memory and at least a portion of the processing resource is located on the smart phone.

10. The device of claim 1, wherein the different types of notifications comprise at least one of an audio component, a visual component, and a haptic component, and
  wherein the visual component comprises at least one of a light component, a motion component, a text component, and an image component.

11. The device of claim 1, wherein the different types of notifications includes at least a suppressed notification.

12. The device of claim 1, wherein the sensed user response to the selective communication comprises at least one of:
  ignore;
  visual glance;
  pressing a control;
  tapping the device;
  any movement of device;
  amplitude of device movement;
  duration of interaction; and
  duration of delay before response.

13. The device of claim 1, wherein the prior response of the user to different types of notifications for different types of received inputs in different social contexts includes at least one of a physiologic parameter of the user and an environmental parameter of the user.

14. A wearable electronic device comprising:
  a processor to execute machine readable instructions stored in a non-transitory memory to:
    determine a context indicator in association with a received input, wherein the context indicator includes a social context parameter for a user of the wearable electronic device at a time of the received input and an importance parameter of the received input; and
    select, based on the context indicator and the received input, at least one type of notification from a plurality of different types of notifications; and
    communicate the received input to the user via the selected type of notification,
  wherein the context indicator is at least partially based on a history of behavior of the user regarding the different types of notifications relative to the social context parameter for the user and the importance parameter of the received input.

15. The wearable electronic device of claim 14, wherein the processor is in communication with an external processing resource to at least partially execute the stored machine readable instructions and wherein the non-transitory memory is in communication with an external non-transitory memory to at least partially store the machine readable instructions.

16. The wearable electronic device of claim 14, wherein the social context parameter for the user includes a physiologic parameter of the user and an environmental parameter of the user.

17. A wearable wristwatch comprising:
a time-keeping display portion;
a non-time-keeping display portion; and
a processor to execute machine readable instructions stored in a non-transitory memory to:
determine a social context indicator in association with a received input, wherein the social context indicator is based on a social context of a user at a time of the received input and prior response of the user to different types of notifications for different types of received inputs in different social contexts;
select, based on the received input, the social context of the user, and the social context indicator, at least one type of notification from the different types of notifications; and
selectively communicate the received input to the user via the selected type of notification using the non-time-keeping display portion,
wherein the social context indicator establishes context-appropriate communication of the received input.

18. The wearable electronic device of claim 17, the instructions to:
sense for different types of single user response to the selective communication of the received input; and
receive feedback regarding the sensible different types of single user response to at least partially determine future instances of the social context indicator.

19. The wearable wristwatch of claim 17, wherein the social context of the user is based on a physiologic parameter of the user and an environmental parameter of the user.

20. The wearable wristwatch of claim 17, wherein the prior response of the user to different types of notifications for different types of received inputs in different social contexts includes a physiologic parameter of the user and an environmental parameter of the user.

\* \* \* \* \*